United States Patent [19]

Ho

[11] 4,304,942
[45] Dec. 8, 1981

[54] PRODUCING SUBSTITUTED 2-CYCLOPENTENONES

[75] Inventor: T. L. Ho, Jacksonville, Fla.

[73] Assignee: SCM Corporation, New York, N.Y.

[21] Appl. No.: 152,137

[22] Filed: May 21, 1980

[51] Int. Cl.³ .............................................. C07C 45/45
[52] U.S. Cl. .................................. 568/354; 560/156; 562/553
[58] Field of Search ................ 560/156; 568/354, 355, 568/356, 350; 562/553

[56] References Cited

U.S. PATENT DOCUMENTS 2,554,831 5/1951 Kloetzel .............................. 560/156
3,577,455 5/1971 Jones et al. .......................... 560/156

FOREIGN PATENT DOCUMENTS 894638 5/1959 United Kingdom ................ 568/354

OTHER PUBLICATIONS

Fakin et al., Chem. Abst., vol. 87, #200711r (1977).
Tishchenko et al., Chem. Abst., vol. 88, #220772 (1978).
Sisido et al., J. Org. Chem., vol. 29, pp. 904–907 (1964).
Tsuji et al., Tetrahedron, vol. 39, pp. 3741–3743 (1979).
Ho, Synthetic Comm., vol. 4, #5, pp. 285–287 (1974).
Bellasio et al., Chem. Abst., vol. 85, #177173q (1976).

Primary Examiner—Natalie Trousof
Assistant Examiner—James H. Reamer
Attorney, Agent, or Firm—Robert A. Sturges; Merton H. Douthitt

[57] ABSTRACT

A process is provided for producing substituted 2-cyclopentenones represented by the general formula:

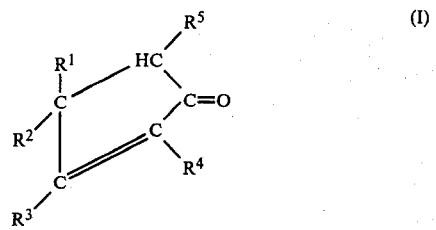

where $R^1$, $R^2$, $R^3$, $R^4$, and $R^5$ are hydrogen or lower aliphatic hydrocarbyl groups. The process comprises treating a nitroalkane with a substituted acrylic acid ester in the presence of a base, followed by saponification, to yield a substituted 4-nitropentanoic acid which acid is then treated with strong acid under dehydrative conditions to yield the subject 2-cyclopentenone.

12 Claims, No Drawings

PRODUCING SUBSTITUTED 2-CYCLOPENTENONES

This invention relates to a process for producing substituted cyclopentenones.

More specifically, the invention relates to a process for producing cyclopentenones which may be represented by the following formula:

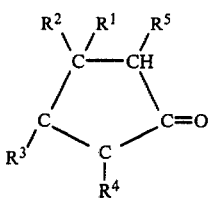

where $R^1$, $R^2$, $R^3$, $R^4$, and $R^5$ can be hydrogen or lower aliphatic hydrocarbyl moieties in varying combinations to provide substituted cyclopentenones which are important in the production of perfumes, insecticides, and pharmaceuticals.

BACKGROUND OF THE INVENTION AND PRIOR ART

A known earlier method for the preparation of dihydrojasmone and its homologues is found in the Journal of Organic Chemistry, 29, 904, (1964), Sisido et al. This route involves the reaction of ethyl gamma, gamma-dialkyl glycidates with sodium malonate to obtain lactonic intermediates, followed by hydrolysis of the lactone diesters formed in the first step to give diacids, decarboxylation of the diacids to paraconic acid, then conversion to the dihydrojasmone analogue by action of polyphosphoric acid on the paraconic acid.

The present invention is an improvement on the above prior art method in that it avoids the use of the glycidyl compound. This class of compounds is known for its toxic nature (see Sax, "Dangerous Properties of Industrial Materials", 5th Edition, (1974) and its carcinogenic possibilities. Accordingly, such materials pose a safety problem in commercial production. This problem is avoided according to the present invention by starting with nitroalkanes and acrylic esters, or substituted gamma nitropentanoic acids.

BRIEF STATEMENT OF INVENTION

It has been found that at least two commercially significant 2-cyclopentenones, e.g., jasmone and dihydrojasmone, as well as the analogues thereof, may be produced by reacting a nitroalkane with a substituted acrylic ester. The nitroalkane may be represented by the general formula:

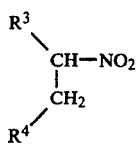

where $R^3$ and $R^4$ are independently selected from hydrogen and lower aliphatic hydrocarbyl, e.g., $C_1$-$C_6$ aliphatic hydrocarbyl, groups. The acrylate may be represented by the general formula:

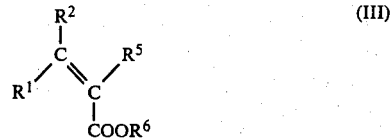

where $R^1$, $R^2$, $R^5$, and $R^6$ are independently selected from hydrogen and $C_1$-$C_6$ aliphatic hydrocarbyl groups. The reactants (II) and (III) are reacted in the liquid phase in the presence of a basic catalyst. The reaction results in addition of the carbon atom bearing the nitro group to the beta-carbon of the acrylate to give a substituted gamma nitropentanoic ester. This product may be represented by the formula:

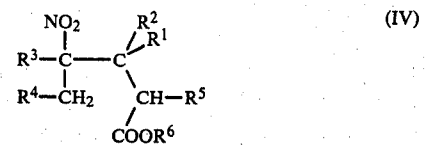

where $R^1$, $R^2$, $R^3$, $R^4$, $R^5$, and $R^6$ have the meanings ascribed above.

Saponification of (IV) results in the carboxylic acid the corresponding nitro-carboxylic acid:

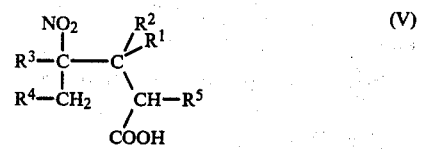

Under strong acid dehydrative conditions the desired substituted 2-cyclopentenones (I) are formed. Dehydrojasmone where $R^1$ is hydrogen, $R^4$ is —$CH_2C\equiv CCH_2CH_3$, $R^3$ is —$CH_3$, $R^2$ and $R^5$ are each hydrogen, is the result of dehydrative cyclization. Dehydrojasmone, a precursor of cis-jasmone, has the following structural formula:

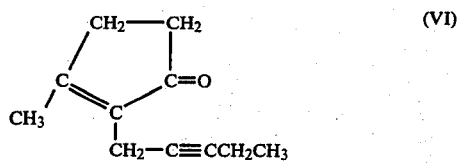

Another 2-cyclopentenone (I) which can be produced by the process hereof is dihydrojasmone where $R^1$ is hydrogen, $R^4$ is —$(CH_2)_4$—$CH_3$, $R^3$ is —$CH_3$ and $R^2$ and $R^5$ are each hydrogen. Again, the nature of the $R^4$ contributing material (the allylic alcohol) determines the nature of the resulting cyclopentenone. Dihydrojasmone may be represented by the formula:

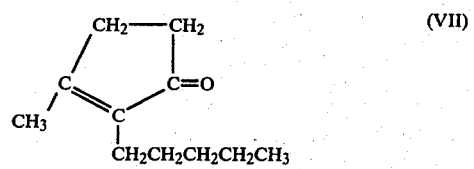

and the analogues and homologues thereof. Specific examples of $C_1$-$C_6$ aliphatic hydrocarbyl groups useful as $R^1$, $R^2$, $R^3$, $R^4$, $R^5$, and $R^6$ herein include methyl, ethyl, n-propyl, isopropyl, n-butyl, sec.-butyl, isobutyl, amyl, isoamyl, n-hexyl, isohexyl, cyclohexyl, and the like.

Similar results are secured by starting with an appropriate substituted nitropentanoic acid (IV).

DETAILED DESCRIPTION AND SPECIFIC ILLUSTRATIVE EXAMPLES

As indicated above, the process for making 2-cyclopentenones constituting the present invention begins with the step of chemically adding, by a Michael addition reaction, a secondary nitroalkane containing at least two carbon atoms to an α,β-unsaturated carboxylic acid ester. This reaction is carried out in the presence of a base as a catalyst, e.g., an alkali metal hydroxide, e.g., sodium hydroxide, lithium hydroxide, or potassium hydroxide, pyridine, quaternary ammonium hydroxide, e.g., benzyl trimethyl ammonium hydroxide. The resulting ester is then saponified by any suitable reaction, e.g., use of a sufficient amount of one of the alkali metal hydroxides or carbonates, to cleave the ester into the carboxylic acid salt. Upon treatment with a strong acid, e.g., a mineral acid such as, $H_2SO_4$, $H_3PO_4/P_2O_5$ $P_2O_5/CH_3SO_3$ H, the carboxylic acid forms an acylium ion which is intercepted by the —$NO_2$ group. Second stage ionization, elimination of nitrous acid then generates the unsaturated species. Cyclization of such species is well known.

Schematically summarizing the reactions of the present invention, the following schemes are given:

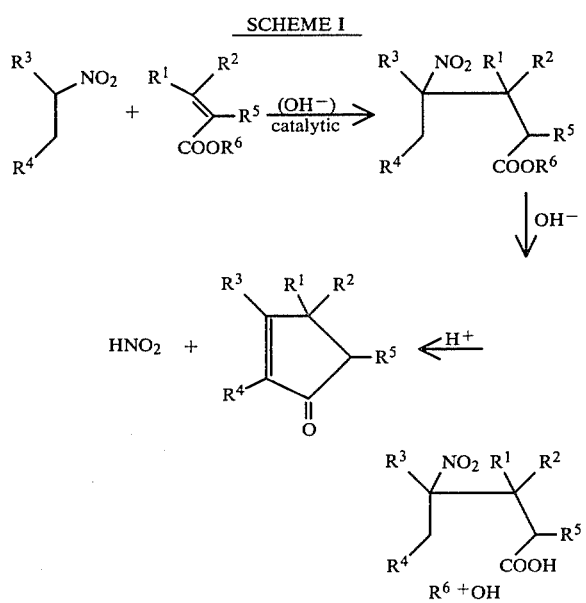

The cyclization step which is utilized in this invention contemplates the use of a strong acid and/or a dehydration system, the carboxylic acid forms the acylium ion which is intercepted by the nitro group. As indicated above, further ionization and elimination of nitrous acid then yields the unsaturated acylium species.

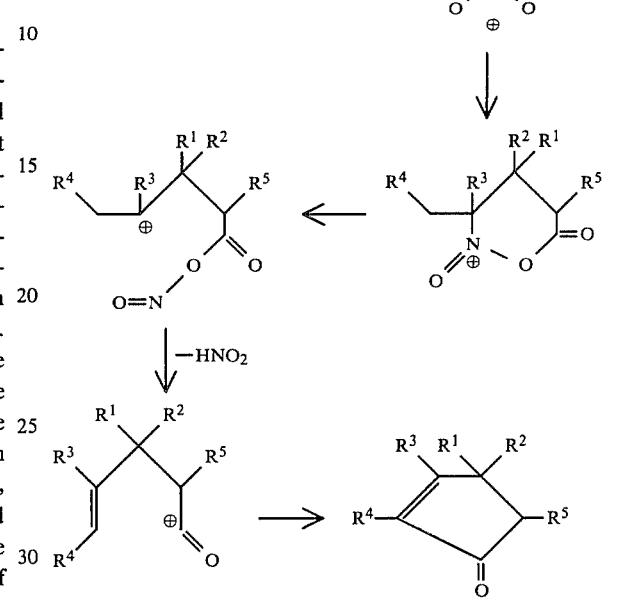

This scheme has been carried out and 2-cyclopentenones have been recovered. In particular, jasmone, dihydrojasmone (a perfumery compound) and 3-methyl-2-cyclopentenone have been synthesized. The latter compound is conveniently converted into methyl cyclopentenolone, synthetic maple syrup flavor.

The Michael addition reaction (Scheme I) is conveniently carried out in the liquid phase at a temperature elevated above room temperature, e.g., 80° to 120° C., with stirring. Conventional saponification and acidification techniques may be used to recover the carboxylic acid. Dehydrative cyclization is the same as disclosed in commonly owned Ser. No. 152,138, filed: 5/21/80.

Specific examples of secondary nitroalkanes useful herein include nitropropane, nitrobutane, nitropentane, nitrohexane, nitrooctane, nitrodecane, etc. Thus, the nitroalkane may contain from 3 to 10 carbon atoms with one nitrogroup attached to a secondary C atom.

Specific examples of acrylates useful herein include methyl acrylate, methyl methacrylate, ethyl acrylate, ethyl ethacrylate, ethyl methacrylate, methyl crotonate, methyl-β, β-dimethyl acrylate, methyl hexen-2-oate, and the like.

With respect to the cyclization reaction, water is conveniently removed, preferably under the influence of a mineral acid anhydride, e.g., $P_2O_5$, polyphosphoric acid, pyrophosphoric acid, etc. Upon removal of water the carboxylic acid cyclizes and forms the 2-cyclopentenone. A catalyst for cyclization, such as a sulphuric acid, methane sulfonic acid, may be used to enhance the cyclization reaction. If dehydration conditions are created as by using a high boiling solvent or vacuum, for example, then catalytic amounts can be used which are less than 5% by weight.

A full understanding of the present invention can be had by reference to the following specific examples which are intended to illustrate to those skilled in the art the procedural steps involved in the subject process, but which are not intended to limit the invention to the scope thereof.

EXAMPLE I

Part A

A mixture of 30 grams of 2-nitropropane and 3.3 mls. of Triton ® B (benzyl trimethylammonium hydroxide; a trademark of the Rohm and Haas Company) in 15 mls. of dioxane was placed in a 200 ml. flask. The mixture was warmed to 70° C. while being stirred. Next, 33 gms. of ethyl acrylate were added to the mixture over a 15-minute period. Following the addition of the ethyl acrylate, the mixture was heated for 16 hours at 100° C. The mixture was cooled, acidified with aqueous hydrochloric acid, and extracted with dichloromethane. Evaporation and distillation of the solvent yielded 62 gms. of the reaction product, ethyl 4-methyl-4-nitropentanoate. This amount of product represented a 97% yield.

Part B

A mixture comprising 18.9 gms. of the reaction product from Part A, ethyl 4-methyl-4-nitropentanoate, 15 gms. of sodium carbonate, and 150 mls. of water was placed in a 250 ml. reaction vessel and heated to reflux for 18 hours. The temperature of reflux was ~100° C. After cooling to room temperature, 25° C., the reaction mixture was acidified with hydrochloric acid and then extracted with dichloromethane. The extracted portion of the reaction mixture yielded 16 gms. of 4-methyl-4-nitropentanoic acid. This amount represented a 100% yield.

Part C

Into 200 gms. of a 1:10 solution of phosphorus pentoxide:methanesulfonic acid, was added 3.0 gms. of a reaction product from Part B, 4-methyl-4-nitropentanoic acid. The solution was stirred at room temperature for 40 hours and then was poured into 400 mls. of water. The reaction mixture was then extracted with dichloromethane to give 1.6 gms. of the desired product, 3-methyl-2-cyclopentenone.

EXAMPLE II

Part A

A mixture of 11.3 gms. of nitrocyclohexane, 1 ml. of Triton ® B, and 10 gms. of ethyl acrylate in 5 mls. of dioxane, was placed in a 50 ml. reaction vessel and was heated for 4 hours at 100° C. After cooling, the reaction mixture was dissolved in dichloromethane, washed with dilute hydrochloric acid, and distilled to yield 16.2 gms. of ethyl 3-(1'-nitrocyclohexyl) propionate. This amount of the ester product represented a 76% yield.

Part B

A mixture of 5 gms. of the reaction product from Part A, ethyl 3-(1-nitrocyclohexyl) propionate and 7.5 mls. of 20% sodium hydroxide solution was stirred in a 25 ml. reaction flask for 16 hours at room temperature, 25° C. Next, the reaction mixture was added to 50 mls. of water, washed with pentane, followed by acidification with hydrochloric acid. The desired product, 3-(1'-nitrocyclohexyl) proprionic acid was collected by precipitation. The 4.2 gms. of product collected represented a 97% yield.

Part C

A 2-gm. amount of the reaction product from Part B, 3-(1'-nitrocyclohexyl) proprionic acid, was stirred into 35 gms. of polyphosphoric acid. The mixture was then heated at 100° C. for 15 minutes. After cooling, the reaction mixture was poured into water, extracted with dichloromethane, and the desired ketone product was isolated by evaporation of the extract. The 0.8 gms. of 5,6,7,8-tetrahydroindan-1-one represented a 59% yield of the desired ketone product.

EXAMPLE III

A mixture of 2.2 gms. of 4-methyl-4-nitrodecanoic acid and 40 gms. of polyphosphoric acid was heated for 1 hours at a temperature of 100° C. After cooling to room temperature, the reaction mixture was poured into ice water and then extracted with methylene chloride. The extracted layer was washed with a sodium bicarbonate solution and with water. After evaporation of the organic layer from the washed extract, the oil residue was analyzed by chromatography carried out on alumina. The product was dihydrojasmone. The 0.95 gms. of product obtained represented a 54% yield.

What is claimed:

1. A process for preparing a 2-cyclopentenone which comprises the steps of chemically adding an alpha,beta-unsaturated aliphatic carboxylic acid ester to a secondary nitroalkane containing at least 2 carbon atoms in the liquid phase and in the presence of a basic catalyst selected from an alkali metal hydroxide, pyridine, and a quaternary ammonium hydroxide to form a nitroalkanoate ester, converting said nitroalkanoate ester into the corresponding carboxylic acid by saponification and acidification and dehydratively cyclizing said corresponding acid in the presence of a strong mineral acid to form said 2-cyclopentenone.

2. A process for preparing a 2-cyclopentenone represented by the general formula:

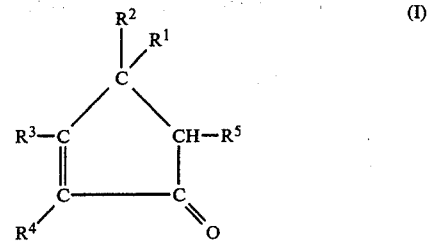

(I)

wherein $R^1$, $R^2$, $R^3$, $R^4$, and $R^5$ are independently selected from hydrogen and $C_1$–$C_{10}$ aliphatic hydrocarbyl groups; which comprises the steps of chemically adding an alpha, beta-unsaturated aliphatic carboxylic acid ester represented by the general formula:

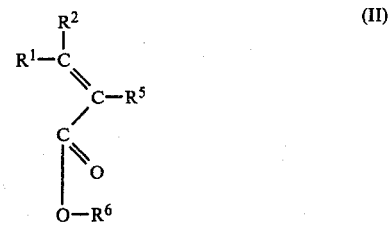

(II)

where $R^2$ and $R^5$ have the meaning defined above, and $R^6$ is a $C_1$–$C_6$ aliphatic hydrocarbyl group, to a secondary nitroalkane represented by the general formula:

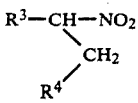
(III)

where $R^3$ and $R^4$ are as defined above, in the liquid phase and in the presence of a basic catalyst selected from an alkali metal hydroxide, pyridine, and a quaternary ammonium hydroxide to yield a nitroalkanoate ester represented by the general formula:

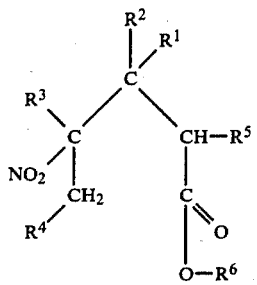
(IV)

wherein $R^1$, $R^2$, $R^3$, $R^4$, $R^5$, and $R^6$ are as defined above, converting said nitroalkanoate ester (IV) to the corresponding carboxylic acid by replacing the $R^6$ radical with hydrogen by saponification and acidification; and dehydratively cyclizing said corresponding acid in the presence of a strong mineral acid to yield said 2-cyclopentenone (I) of formula above.

3. The process claims 1 or 2 wherein said $\alpha,\beta$-unsaturated carboxylic acid ester (II) is an ester of acrylic acid.

4. The process of claims 1 or 2 wherein said secondary nitroalkane is a $C_3$–$C_8$ nitroalkane.

5. The process of claims 1 or 2 wherein said $\alpha,\beta$-unsaturated carboxylic acid ester (II) is ethyl acrylate.

6. The process of claims 1 or 2 wherein said $\alpha,\beta$-unsaturated carboxylic acid ester (II) is ethyl acrylate, said secondary nitroalkane (III) is 2-nitro-octane, and the resultant product (I) is dihydrojasmone.

7. The process of claims 1 or 2 wherein said $\alpha,\beta$-unsaturated carboxylic acid ester (II) is ethyl acrylate, said secondary nitroalkane (III) is 2-nitropropane, and the resultant product (I) is 3-methyl-2-cyclopentenone.

8. The process of claims 1 or 2 wherein said nitroalkanoate ester is converted to said corresponding acid by saponification.

9. The process for preparing a 2-cyclopentenone which comprises treating a nitropentanoic acid with a strong mineral acid under dehydrative conditions to effect cyclizing to form a 2-cyclopentenone.

10. A process for preparing a 2-cyclopentenone which comprises the step of dehydratively cyclizing a compound having the general formula:

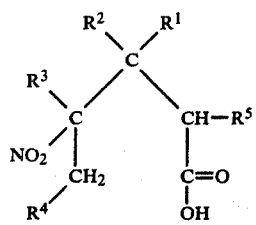
(IV)

wherein $R^1$, $R^2$, $R^3$, $R^4$, and $R^5$ are independently selected from hydrogen and $C_1$–$C_{10}$ aliphatic hydrocarbyl groups, with a strong mineral acid under dehydrative conditions to effect cyclization and form a 2-cyclopentenone.

11. A process as defined in claims 9 or 10 in which the mineral acid is polyphosphoric acid.

12. A process as defined in claims 11 or 10 in which the dehydrative conditions result from the addition of $P_2O_5$-methanesulfonic acid.

* * * * *